(12) United States Patent
Gelb et al.

(10) Patent No.: US 6,799,076 B2
(45) Date of Patent: Sep. 28, 2004

(54) COATED ELECTRODE AND METHOD OF MAKING A COATED ELECTRODE

(75) Inventors: Allan S. Gelb, Elkridge, MD (US); Bruce D. Platt, Reisterstown, MD (US)

(73) Assignee: Greatbatch-Hittman, Inc., Columbia, MD (US)

( * ) Notice: Subject to any disclaimer, the term of this patent is extended or adjusted under 35 U.S.C. 154(b) by 35 days.

(21) Appl. No.: 09/730,314

(22) Filed: Dec. 5, 2000

(65) Prior Publication Data

US 2001/0032005 A1 Oct. 18, 2001

Related U.S. Application Data

(60) Provisional application No. 60/169,370, filed on Dec. 7, 1999.

(51) Int. Cl.[7] .................................................. A61N 1/05
(52) U.S. Cl. ......................... 607/121; 600/395; 607/9; 427/255; 427/394
(58) Field of Search ............................... 600/374, 375, 600/395; 427/2.24, 255.394, 255.7; 607/9, 36, 119, 121

(56) References Cited

U.S. PATENT DOCUMENTS

| | | | | |
|---|---|---|---|---|
| 4,440,178 A | * | 4/1984 | Bussard et al. | 607/121 |
| 4,584,079 A | * | 4/1986 | Lee et al. | 204/192.13 |
| 4,602,637 A | | 7/1986 | Elmqvist et al. | 128/419 |
| 4,603,704 A | | 8/1986 | Mund et al. | 128/784 |
| 4,611,604 A | | 9/1986 | Botvidsson et al. | 128/784 |
| 4,679,572 A | | 7/1987 | Baker, Jr. | 128/786 |
| 4,784,160 A | * | 11/1988 | Szilagyi | 427/446 |
| 4,919,135 A | * | 4/1990 | Phillips et al. | 607/121 |
| 5,181,526 A | * | 1/1993 | Yamasaki | 607/121 |
| 5,252,181 A | * | 10/1993 | Dutartre et al. | 134/1.1 |
| 5,356,833 A | * | 10/1994 | Maniar et al. | 438/656 |
| 5,427,631 A | * | 6/1995 | Johansson et al. | 148/238 |
| 5,587,200 A | * | 12/1996 | Lorenz et al. | 427/2.24 |
| 5,609,611 A | | 3/1997 | Bolz et al. | |
| 5,622,607 A | * | 4/1997 | Yamazaki et al. | 204/192.15 |
| 5,645,580 A | * | 7/1997 | Moaddeb et al. | 607/122 |
| 5,683,443 A | * | 11/1997 | Munshi et al. | 607/119 |
| 5,953,633 A | * | 9/1999 | Chen et al. | 438/683 |
| 5,963,827 A | * | 10/1999 | Enomoto et al. | 438/629 |
| 5,964,794 A | * | 10/1999 | Bolz et al. | 607/121 |
| 6,025,205 A | * | 2/2000 | Park et al. | 438/3 |
| 6,430,447 B1 | | 8/2002 | Chitre et al. | |
| 6,430,448 B1 | | 8/2002 | Chitre et al. | |

* cited by examiner

Primary Examiner—Ramesh Krishnamurthy
(74) Attorney, Agent, or Firm—Michael F. Scalise

(57) ABSTRACT

An electrode having a substrate with a first layer covering at least a portion of the substrate, and a second layer covering at least a portion of the first layer is disclosed. The first layer includes a porous layer consisting of a carbide, nitride or carbonitride of at least one of the metals titanium, vanadium, zirconium, niobium, molybdenum, hafnium, tantalum or tungsten. The second layer includes iridium.

In a method according to the present invention, a substrate is provided. A first layer is provided over at least a portion of the substrate, and a second layer is provided over at least a portion of the first layer. The first layer includes a layer consisting of a carbide, nitride or carbonitride of at least one of the metals titanium, vanadium, zirconium, niobium, molybdenum, hafnium, tantalum or tungsten. The second layer includes iridium.

13 Claims, 4 Drawing Sheets

PROVIDE A SUBSTRATE. — 100

ETCH THE SUBSTRATE. — 103

PROVIDE A FIRST OVER AT LEAST A PORTION OF THE SUBSTRATE — 106

PROVIDE A SECOND LAYER OVER A LEAST A PORTION OF THE FIRST LAYER. — 109

FIG. 2

COATED ELECTRODE AND METHOD OF MAKING A COATED ELECTRODE

CROSS CLAIM TO RELATED APPLICATION

Priority is hereby claimed to U.S. Provisional Patent Application No. 60/169,370 filed on Dec. 7, 1999, and is hereby incorporated by this reference.

BACKGROUND OF THE INVENTION

FIELD OF THE INVENTION

The present invention relates generally to coated electrodes and methods of making such electrodes.

SUMMARY OF THE INVENTION

The present invention includes an electrode having a substrate with a first layer covering at least a portion of the substrate, and a second layer covering at least a portion of the first layer. The first layer includes a porous layer consisting of a carbide, nitride or carbonitride of at least one of the metals titanium, vanadium, zirconium, niobium, molybdenum, hafnium, tantalum or tungsten. The second layer includes iridium.

In a method according to the present invention, a substrate is provided. A first layer is provided over at least a portion of the substrate, and a second layer is provided over at least a portion of the first layer. The first layer includes a porous layer consisting of a carbide, nitride or carbonitride of at least one of the metals titanium, vanadium, zirconium, niobium, molybdenum, hafnium, tantalum or tungsten. The second layer includes iridium.

BRIEF DESCRIPTION OF THE DRAWINGS

For a fuller understanding of the nature and objects of the invention, reference should be made to the following detailed description taken in conjunction with the accompanying drawings, in which:

FIG. 2 illustrates a method according to the present invention;

BEST MODE FOR CARRYING OUT THE INVENTION

Figure 1:
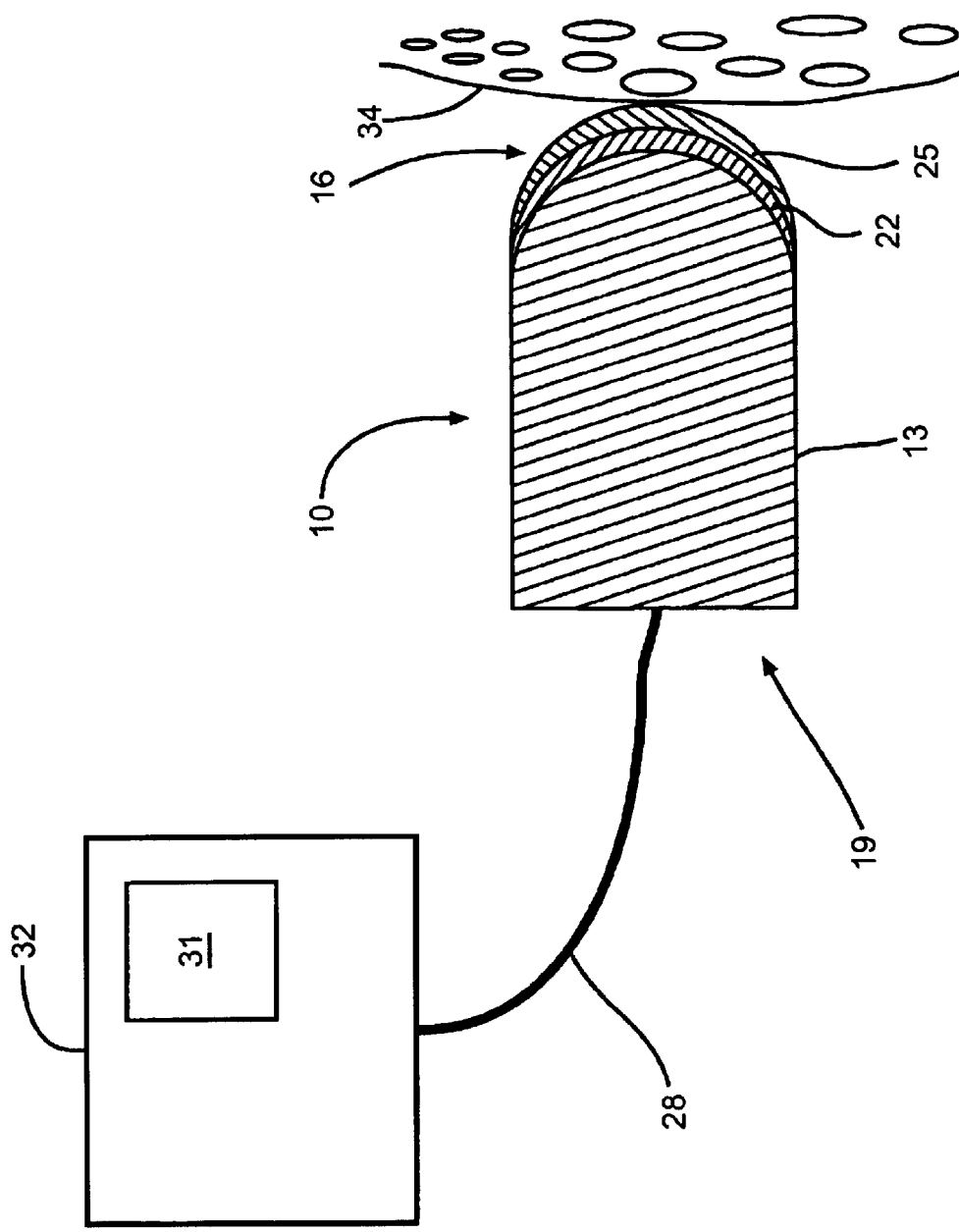
FIG. 1 is a cross sectional side view of an electrode according to the present invention.

FIG. 1 shows an electrode 10 according to the present invention. The electrode 10 has a substrate 13 with a first end 16 and a second end 19. The substrate 13 may include platinum, iridium or both. For example, the substrate may be approximately 90% platinum and approximately 10% iridium. Other bio-compatible metals, such as titanium, may be suitable materials for the substrate.

The first end 16 has a first layer 22 and a second layer 25. The first layer 22 includes a porous layer of a carbide, nitride or carbonitride of at least one of the metals titanium, vanadium, zirconium, niobium, molybdenum, hafnium, tantalum or tungsten. The metals forming the carbides, nitrides and carbonitrides are all elements of the fourth through sixth sub-groups of the periodic system and thus include the transition metals. Carbides and nitrides of these transition metals include titanium carbide, titanium nitride, zirconium carbide and tantalum nitride. The first layer may further include other layers such as a layer of titanium. The first layer 22 may contact a portion of the substrate 13.

The second layer 25 covers at least a portion of the first layer 22, and the second layer 25 may contact the first layer 22. The second layer 25 may be an outer surface of the electrode 10. The second layer 25 includes iridium, iridium oxide, or both.

In use, the second end 19 of the electrode 10 receives electricity to be delivered to the first end 16. The second end 19 may be electrically connected via an electrical conductor 28 to an energy source 31, such as an electrical pulse generator of a cardiac pacemaker 32. When connected to a cardiac pacemaker 32, the first end 16 senses signals from the heart and delivers the signals to the second end 19 where the signals are transmitted to the cardiac pacemaker 32 via the electrical conductor 28.

The present invention includes a cardiac pacing lead assembly. Such an assembly has an electrode, like that described above, wherein the second layer 25 is electrically connected to excitable cardiac tissue 34. The present invention also includes a cardiac pacemaker 32 having a pacing lead assembly connected to an electrical pulse generator, like those described above.

FIG. 2 illustrates aspects of a method of making an electrode according to the present invention. In the method, a substrate, such as that described above, is provided 100. The substrate may be etched 103 to provide an etched substrate. Etching 103 the substrate may be performed in a sputter chamber by radio frequency ("RF") sputter etching. In one embodiment of the present invention, RF sputter etching occurs in an argon rich atmosphere.

A first layer is provided 106 over at least a portion of the substrate. To provide at least part of the first layer, an RF bias may be applied to the substrate while DC sputtering with titanium in the sputter chamber.

As noted above, the first layer includes a porous layer consisting of a carbide, nitride or carbonitride of at least one of the metals titanium, vanadium, zirconium, niobium, molybdenum, hafnium, tantalum or tungsten. For example, to provide a titanium nitride layer, DC sputtering with titanium may be carried out in a nitrogen rich atmosphere. In an embodiment of such a method, DC sputtering with titanium in a nitrogen rich atmosphere occurs for a period of time while an RF bias is applied to the electrode, for example via the substrate, and then for a period of time while no RF bias is applied to the electrode. Other embodiments of the present invention do not apply an RF bias to the electrode while sputtering with titanium in a nitrogen rich atmosphere.

A second layer is provided 109 on at least a portion of the first layer to provide the electrode. The second layer includes iridium, iridium oxide, or both, and may be provided using the sputter chamber.

An example of a method according to the present invention, begins by providing a clean 90% platinum 10% iridium substrate. The substrate may be cleaned by sonicating the substrate with detergent, and rinsing the substrate with deionized water. To aid in drying and cleaning, the rinsed substrate may be sonicated with acetone, and rinsed with 2-propanol.

Figure 3:
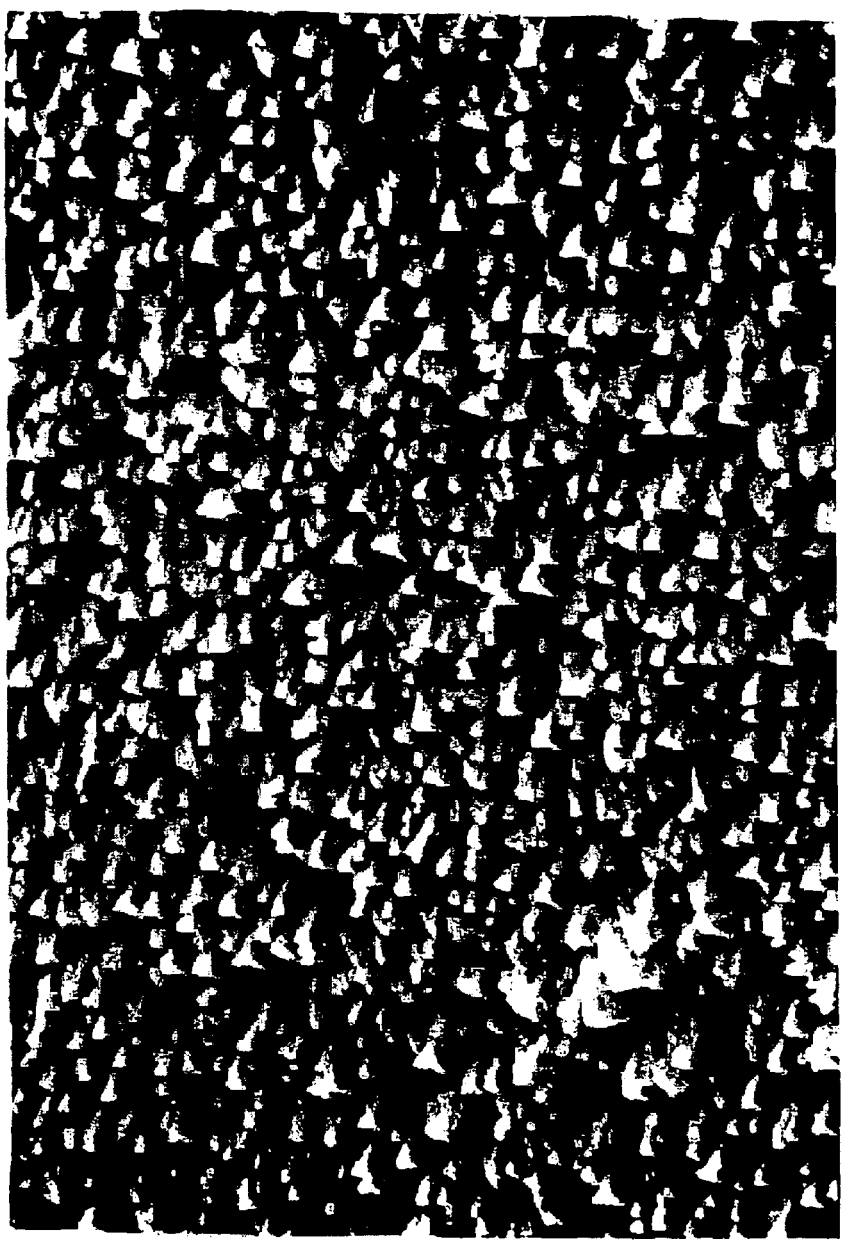
FIG. 3 shows an electron photo micrograph of a first layer according to the present invention.

The cleaned substrate is then placed in a sputter chamber, such as model number 8667 manufactured by Materials Research Corporation located in Orangeburg, N.Y. that has been modified to provide reactive sputtering capabilities. The chamber is evacuated to less than 5 micro torr. The substrate is then RF sputter etched at 500 watts in an atmosphere of 7.0 mtorr of argon for 18 minutes. The etched substrate is then direct current ("DC") sputtered with titanium for 2 minutes at 1 kW, with an RF bias applied to the substrate. Then nitrogen is introduced into the chamber at a combined pressure of 7.5 mtorr. After 18 minutes, the RF bias is removed, and the substrate continues to be sputtered with titanium for several hours at 1 kW. FIG. 3 shows a surface of a titanium-containing layer made according to the present invention.

Figure 4:
FIG. 4 shows an electron photo micrograph of a second layer according to the present invention.

The sputter chamber, with the titanium and titanium nitride coated substrate therein, is then evacuated to less than 5 micro torr. The titanium nitride coated substrate is sputtered with iridium for 30 minutes at 250 W RF. After performing this method, the iridium layer was found to be 0.27 microns thick. When exposed to air, at least some of the iridium may oxidize to form iridium oxide. FIG. 4 shows a surface of an iridium-containing layer made according to the present invention.

It is known that low values of polarization contribute to lower threshold voltages for the pacing function of a cardiac packing electrode and of a defibrillation electrode. Low values of polarization also contribute to increased sensitivity for the sensing function of such electrodes. Low polarization may also contribute to greater efficacy in stimulation of other types of muscle tissue and in the detection of other electrical activity in the body. It is known that titanium nitride can be reactively sputtered to yield a morphology suitable for a low polarization coating on an electrode. Titanium nitride is widely used for electrode coatings, but there are concerns regarding the long-term stability of titanium nitride.

It is also known that iridium (which probably oxidizes to iridium oxide in air and more so after pulsing) or iridium oxide can lower the polarization of an electrode, although generally not to as low a value as titanium nitride. Furthermore, iridium and iridium oxide coatings on electrodes have been shown to prevent the growth of fibrotic tissue around such electrodes. However, neither iridium nor iridium oxide has the very desirable morphology of titanium nitride.

The present invention combines a layer of material selected from the group of a carbide, nitride or carbonitride of at least one of the metals titanium, vanadium, zirconium, niobium, molybdenum, hafnium, tantalum or tungsten, such as titanium nitride, with a layer of iridium, iridium oxide or both. In doing so, the present invention achieves low polarization and prevents the growth of fibrotic tissue. Furthermore, the present invention promotes the long-term stability of the first layer by coating it with a second layer.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method for making an electrode, comprising the steps of:
   a) providing a substrate having a surface to be coated;
   b) etching the substrate in an inert atmosphere;
   c) contacting at least a portion of the etched substrate surface with a first layer consisting of at least one of the metals selected from the group consisting of titanium, vanadium, zirconium, niobium, molybdenum, hafnium, tantalum, and tungsten in an elemental form;
   d) providing the substrate in a nitrogen rich atmosphere;
   e) applying a RF bias to the substrate while DC sputtering a second layer to a least a portion of the first layer, wherein the second layer is selected from the group consisting of a carbide, a nitride, and a carbonitride of the same metal as the at least one metal of the first layer; and
   f) contacting a third layer comprising an iridium-containing material to at least a portion of the second layer to provide the electrode.

2. The method of claim 1 wherein etching the substrate includes RF sputter etching the substrate.

3. The method of claim 1 wherein etching the substrate is performed in an argon rich atmosphere.

4. The method of claim 1, wherein providing the first layer includes DC sputtering with titanium.

5. The method of claim 1, wherein DC sputtering with titanium is performed in an argon rich atmosphere.

6. The method of claim 1, wherein providing the second layer includes DC sputtering in a nitrogen rich atmosphere.

7. The method of claim 1, wherein providing the third layer is performed using an RF sputter chamber.

8. A method for making an electrode, comprising the steps of:
   a) providing a substrate;
   b) applying an RF bias to the substrate;
   c) DC sputtering a first layer contacted to at least a portion of the substrate being subject to the RF bias to provide a coated substrate, the first layer comprised of a material selected from the group consisting of a carbide, a nitride, and a carbonitride of at least one of the metals selected from the group consisting of titanium, vanadium, zirconium, niobium, molybdenum, hafnium, tantalum, and tungsten; and
   d) providing a second layer comprising an iridium-containing material covering at least a portion of the first layer to provide the electrode.

9. A method for making an electrode, comprising the steps of:
   a) providing a substrate contained in a nitrogen rich atmosphere;
   b) applying an RF bias to the substrate;
   c) DC sputtering a first layer contacted to at least a portion of the substrate being subjected to the RF bias in the nitrogen rich atmosphere to provide a coated substrate, the first layer comprised of a material selected from the group consisting of a carbide, a nitride, and a carbonitride of at least one of the metals selected from the group consisting of titanium, vanadium, zirconium, niobium, molybdenum, hafnium, tantalum, and tungsten; and
   d) providing a second layer comprising an iridium-containing material contacting at least a portion of the first layer to provide the electrode.

10. A method for making an electrode, comprising the steps of:
   a) providing a substrate contained in a nitrogen rich atmosphere;
   b) applying an RF bias to the substrate;
   c) DC sputtering a first layer contacting at least a portion of the substrate being subjected to the RF bias in the nitrogen rich atmosphere, the first layer comprised of a first material selected from the group consisting of a carbide, a nitride, and a carbonitride of at least one of the metals selected from the group consisting of titanium, vanadium, zirconium, niobium, molybdenum, hafnium, tantalum, and tungsten;

d) DC sputtering a second layer contacting at least a portion of the first layer, the second layer being applied in the nitrogen rich atmosphere and comprised of a second material selected from the group consisting of a carbide, a nitride, and a carbonitride of at least one of the metals selected from the group consisting of titanium, vanadium, zirconium, niobium, molybdenum, hafnium, tantalum, and tungsten, wherein the second layer is applied without the substrate being subjected to the RF bias; and e) providing a third layer comprising an iridium-containing material contacting at least a portion of the second layer to provide the electrode.

11. A method for making an electrode, comprising the steps of:

a) providing a substrate having a surface to be coated;

b) contacting at least a portion of the substrate surface with a first layer consisting of at least one of the metals selected from the group consisting of titanium, vanadium, zirconium, niobium, molybdenum, hafnium, tantalum, and tungsten in an elemental form;

c) contacting a second layer to at least a portion of the first layer, wherein the second layer is selected from the group consisting of a carbide, a nitride, and a carbonitride of the same metal as the at least one metal of the first layer and is contacted to the first layer by DC sputtering in a nitrogen rich atmosphere while an RF bias is applied to the substrate; and d) contacting a third layer comprising an iridium-containing material to at least a portion of the second layer to provide the electrode.

12. A method for making an electrode, comprising the steps of:

a) providing a substrate having a surface to be coated;

b) contacting at least a portion of the subtrate surface with a first layer consisting of at least one of the metals selected from the group consisting of titanium, vanadium, zirconium niobium, molybdenum, hafnium, tantalum, and tungsten in an elemental form;

c) contacting a second layer to at least a portion of the first layer, wherein the second layer is selected from the group consisting of a carbide, a nitride, and a carbonitride of the same metal as the at least one metal of the first layer and is contacted to the first layer by DC sputtering in a nitrogen rich atmosphere for a period of time while an RF bias is applied to the substrate, and then for a period of time while no RF bias is applied to the substrate; and d) contacting a third layer comprising an iridium-containing material to at least a portion of the second layer to provide the electrode.

13. A method for making an electrode, comprising the steps of:

a) providing a substrate having a surface to be coated;

b) etching the substrate in an inert atmosphere;

c) contacting at least a portion of the etched substrate surface with a first layer consisting of at least one of the metals selected from the group consisting of titanium, vanadium, zirconium, niobium, molybdenum, hafnium, tantalum, and tungsten in an elemental form;

d) providing the substrate in a nitrogen rich atmosphere;

e) applying a RF bias to the substrate for a first period of time and then removing the RF bias for a second period all the while DC sputtering a second layer to at least a portion of the first layer, wherein the second layer is selected from the group consisting of a carbide, a nitride, and a carbonitride of the same metal as the at least one metal of the first layer; and f) contacting a third layer comprising an iridium-containing material to at least a portion of the second layer to provide the electrode.

* * * * *